United States Patent [19]

Kaulen et al.

[11] Patent Number: 4,855,438

[45] Date of Patent: Aug. 8, 1989

[54] PROCESS FOR THE PREPARATION OF OPTICALLY ACTIVE 2-HYDROXYETHYLAZOLE DERIVATIVES

[75] Inventors: Johannes Kaulen, Bergisch Gladbach; Dieter Arlt, Cologne; Graham Holmwood, Wuppertal; Wolfgang Krämer, Burscheid, all of Fed. Rep. of Germany

[73] Assignee: Bayer Aktiengesellschaft, Leverkusen, Fed. Rep. of Germany

[21] Appl. No.: 79,844

[22] Filed: Jul. 30, 1987

[30] Foreign Application Priority Data

Aug. 14, 1986 [DE] Fed. Rep. of Germany ....... 3627673

[51] Int. Cl.[4] .......................................... C07D 249/12
[52] U.S. Cl. .................................................... 548/262
[58] Field of Search ........................................ 548/262

[56] References Cited

FOREIGN PATENT DOCUMENTS 0040345 11/1981 European Pat. Off. .
0052424 5/1982 European Pat. Off. .
0085333 8/1983 European Pat. Off. .
0108995 5/1984 European Pat. Off. .
0135854 4/1985 European Pat. Off. .
0181529 5/1986 European Pat. Off. .

Primary Examiner—Glennon H. Hollrah
Assistant Examiner—Patricia L. Morris
Attorney, Agent, or Firm—Sprung Horn Kramer & Woods

[57] ABSTRACT

A new process for the preparation of an optically active 2-hydroxyethyl-azole derivative of the formula

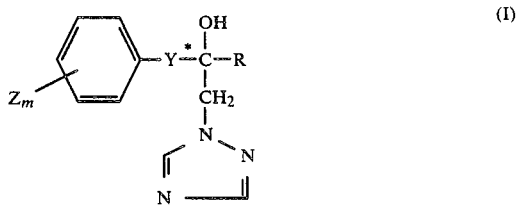

7 Claims, No Drawings

PROCESS FOR THE PREPARATION OF OPTICALLY ACTIVE 2-HYDROXYETHYLAZOLE DERIVATIVES

The invention relates to a new process for the preparation of partly known, optically active 2hydroxyethyl-azole derivatives, which have fungicidal and plant growth-regulating action.

Racemates of numerous 2-hydroxyethyl-azole derivatives have fungicidal and plant growth-regulating properties are already known (cf. EP-OS (European Published Specification) No. 0,040,345, EP-OS (European Published Specification) No. 0,052,424, EP-OS (European Published Specification) No. 0,084,834 and EP-OS (European Published Specification) No. 0,111,711). However, the action of these substances is not always satisfactory, above all at low application mounts.

It is furthermore known that optically active 2-hydroxyethyl-azole derivatives can be prepared by re-acting the basic racemates of oxiranes with optically active sulphonic acids, then separating the resultant mixture of diastereomers into the pure diastereomers, and subsequently reacting the diastereomer which is desired in each case with azole (cf. EP-OS (European Published Specification) No. 181,529 and DE-OS (German Published Specification) No. 3,440,112). However, this process has the disadvantage that the yields of the optically active components which are required in each case are relatively low, since, caused by the separation of the mixture of diastereomers, at least 50% of the material employed cannot be utilized.

It has now been found that optically active 2-hydroxyethyl-azole derivatives of the formula

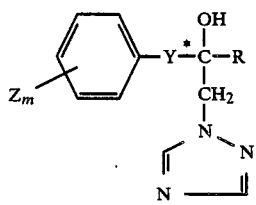

in which
R represents optionally substituted alkyl, optionally substituted cycloalkyl or optionally substituted phenyl,
Y represents the —CH$_2$—CH$_2$—, —CH=CH— or —C≡C— groups, or represents a direct bond,
Z represents halogen, alkyl, cycloalkyl, alkoxy, alkylthio, halogenoalkyl, halogenalkoxy, halogenalkylthio, optionally substituted phenyl, optionally substituted phenoxy, optionally substituted phenylalkyl or optionally substituted phenoxyalkyl, and
m represents the numbers 0, 1, 2 or 3,
can be prepared by
(a) in a first stage, reacting ketones of the formula

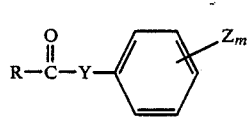

in which

R, Y, Z and m have the abovementioned meaning, with enantiomerically pure oxathianes of the formula

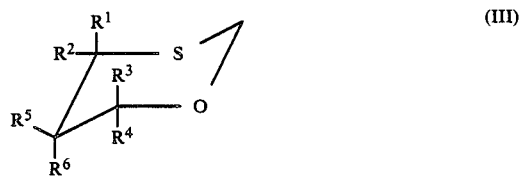

in which
$R^1$, $R^2$, $R^3$, $R^4$, $R^5$ and $R^6$ represent hydrogen or alkyl, but at least one of the radicals represents alkyl, or
$R^4$ and $R^5$, together, represent optionally alkyl-substituted alkanediyl, or
$R^4$ and $R^5$, together with the neighbouring carbon atoms, represent an optionally alkyl-substituted, fused bicyclic hydrocarbon radical,
in the presence of a strongly basic organometallic compound, and in the present of a diluent, at temperatures, between −80° C. and +120° C., then, in a second stage, separating the mixture of diastereomeric compounds of the formulae

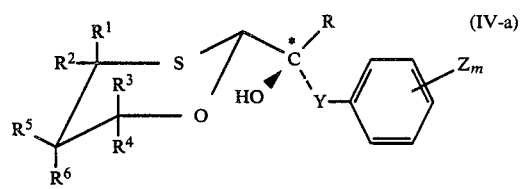

and

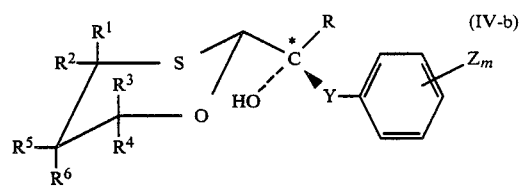

in which
R, $R^1$, $R^2$, $R^3$, $R^4$, $R^5$, $R^6$, Y, Z and m have the abovementioned meaning,
thus obtained as a result of their different physical properties, then, in a third stage, initially reacting the diastereomer of the formula (IV-a) or (IV-b) desired in each case with a reagent which is suitable for the cleavage of oxathiane compounds, in the presence of a diluent and if appropriate in the presence of an acid-binding agent at temperatures between 0° C. and 100° C., and reacting the optically active α-hydroxyaldehydes of the formula

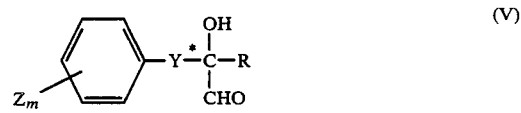

in which
R, Z, Y and m have the abovementioned meaning, produced during this with a reagent which is suitable for the reduction of aldehydes, in the presence of a diluent at temperatures between −20° C. and +100° C., furthermore, in a fourth stage, reacting the optically active diols of the formula $$\underset{Z_m}{\bigodot}-Y-\overset{*}{\underset{CH_2OH}{\overset{OH}{C}}}-R \qquad (VI)$$

in which
R, Y, Z and m have the abovementioned meaning, thus obtained with sulphonic acid derivatives of the formula $$R^7-SO_2-Hal \qquad (VII)$$

in which
R$^7$ represents alkyl, halogenalkyl or optionally substituted phenyl, and
Hal represents halogen,
in the presence of a diluent and in the presence of an acid-binding agent at temperatures between 0° C. and 100° C., and finally, in a fifth stage, reacting the resulting optically active compounds of the formula $$\underset{Z_m}{\bigodot}-Y-\overset{*}{\underset{CH_2-O-SO_2-R^7}{\overset{OH}{C}}}-R \qquad (VIII)$$

in which
R, R$^7$, Y, Z and m have the abovementioned meaning, with triazole salts of the formula $$\text{(IX)}$$

in which
Me represents an alkali metal,
in the presence of a diluent and if appropriate in the presence of an acid-binding agent at temperatures between 20° C. and 150° C., or (b) in a first stage, reacting enantiomerically pure oxathiane ketones of the formula $$\text{(X)}$$

in which
R, R$^1$, R$^2$, R$^3$, R$^4$, R$^5$ and R$^6$ have the abovementioned meaning,
with organometallic compounds of the formula $$\underset{Z_m}{\bigodot}-Y-R^8 \qquad (XI)$$

in which
Y, Z and m have the abovementioned meaning, and
R$^8$ represents an alkali metal, a transition-metal alkylate or a radical of the formula Me$^1$X, in which
Me$^1$ represents an alkaline earth metal or zinc, and
X represents chlorine, bromine or iodine,
in the presence of a diluent at temperatures between −78° C. and +100° C.,
then, in a second stage, initially reacting the diastereomer of the formula $$\text{(IV-b)}$$

in which
R, R$^1$, R$^2$, R$^3$, R$^4$, R$^5$, R$^6$, Y, Z and m have the abovementioned meaning,
produced preferentially, if appropriate after prior chromatographic separation of the diastereomer of the formula (IV-a) produced to a minor extent, with a reagent which is suitable for the cleavage of oxathiane compounds, in the presence of a diluent and if appropriate in the presence of an acid-binding agent at temperatures between 0° C. and 100° C., and then proceeding in the same fashion as in the case of process version (a), or (c) in a first stage, reacting enantiomerically-pure oxathiane ketones of the formula $$\text{(XII)}$$

in which
R$^1$, R$^2$, R$^3$, R$^4$, R$^5$, R$^6$, Y, Z and m have the abovementioned meaning,
with organometallic compounds of the formula $$-R-R^8 \qquad (XIII)$$

in which
R and R$^8$ have the abovementioned meaning,
in the presence of a diluent at temperatures between −78° C. and +100° C.,
then, in a second stage, initially reacting the diastereomer of the formula $$\text{(IV-a)}$$

in which

R, R[1], R[2], R[3], R[4], R[5], R[6], Y, Z and m have the above-mentioned meaning,
produced preferentially, if appropriate after prior chromatographic separation of the diastereomer of the formula (IV-b) produced to a minor extent, with a reagent which is suitable for the cleavage of oxathiane compounds, in the presence of a diluent and if appropriate in the presence of an acid-binding agent at temperatures between 0° C. and 100° C., and then proceeding in the same fashion as in the case of process version (a).

In the present case, only part of the steric arrangement of the individual groups is shown in the formula drawing. Furthermore, asymmetrically substituted carbon atoms are labelled by a (*) in optically active compounds. Apart from the labelled carbon atoms, further asymmetrically substituted carbon atoms may be included.

The course of the process according to the invention is to be described as extremely surprising. Thus, it could not be expected that optically active 2-hydroxyethyl-azole derivatives of the formula (I) could be prepared in very good yield with high selectivity by the method according to the invention. It is also surprising that the diastereomeric compounds produced as intermediates during the reaction can be separated in a simple fashion as a result of their different physical properties. Finally, it could not be predicated that both the R and the S enantiomers of the compounds of the formula (I) could be prepared equally well by the total asymmetrical synthesis according to the invention.

The process according to the invention is distinguished by a number of advantages. Thus, the starting materials and reaction components required are easily accessible and also available in relatively large quantities. Furthermore, the individual reactions and the work-up of the reaction products produced in each case present no difficulties. In addition, it is to be emphasized that the separation, to be carried out, above all, during process version (a), of the diastereomeric compounds is possible without problems using simple means. Furthermore, it is particularly favourable that, in the total asymmetrical synthesis according to process versions (b) and (c), all the starting material is converted into the enantiomer desired in each case whereas, in the previously known processes, half of the material employed cannot be utilized, since these processes are based on a racemate resolution. Finally, a decisive advantage of the process according to the invention comprises that both the R and the S enantiomers can be prepared by appropriate combination of the individual reactions with the aid of the same auxiliary reagents.

If, when carrying out version (a) of the process according to the invention, 2,2-dimethyl-5-(4-chlorophenyl)-pentan-3-one and enantiomerically-pure oxathiane of the formula (III-1) are used as starting materials, silica gel is used as the stationary phase for the chromatographic separation in the second stage, N-chlorosuccinimide and silver nitrate are used as the reagent for the cleavage of the oxathiane compound in the third stage, and lithium aluminium hydride is used for the reduction of the aldehyde in the third stage, chloromethanesulphonic acid is used as a reaction component in the fourth stage, and the sodium salt of triazole is used as a reactant in the fifth stage, the course of the process according to the invention may be illustrated by the following equation:

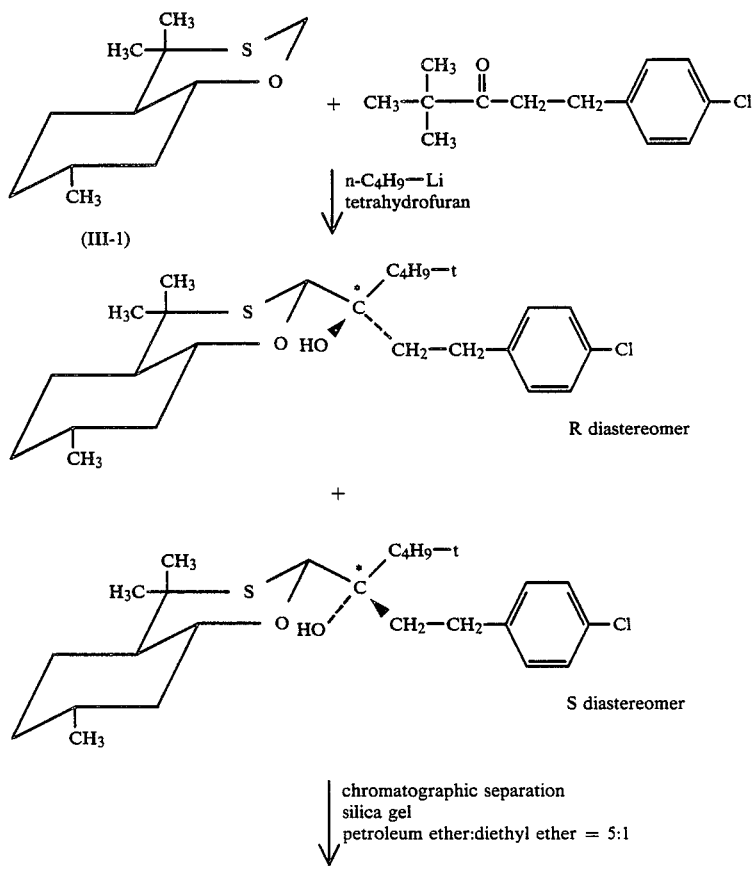

-continued

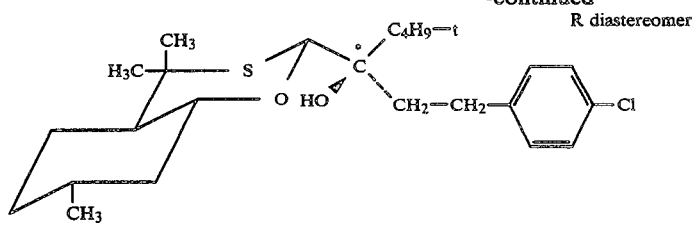
R diastereomer

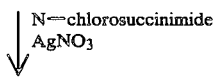

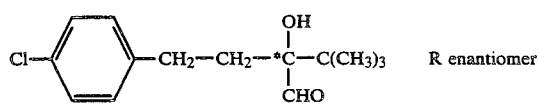
R enantiomer

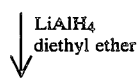

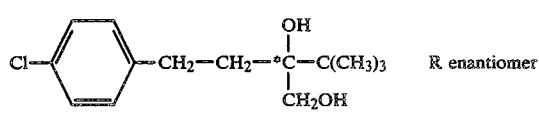
R enantiomer

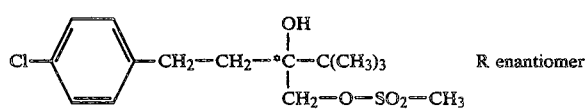
R enantiomer

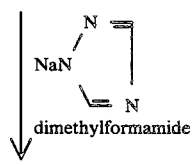

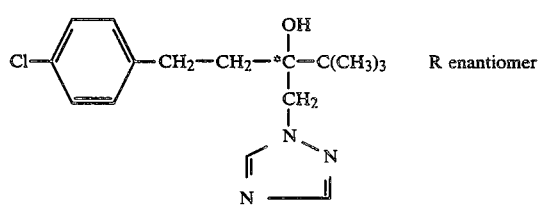
R enantiomer

If, when carrying out version (b) of the process according to the invention, the tert.-butyl ketone which is derived from the enantiomerically-pure oxathiane of the formula (III-1) and 2-(4-chloropheny)-ethyl-magnesium bromide are used as starting materials, N-chlorosuccinimide and silver nitrate are used as the reagent for the cleavage of the S diastereomer, which is produced virtually exclusively, in the second stage, and lithium aluminium hydride is used for the reduction of the aldehyde in the second stage, chloromethane sulphonic acid is used as a reaction component in the third stage, and the sodium salt of triazole is used as the reactant in the fourth stage, the course of the process according to the invention may be illustrated by the following equation:

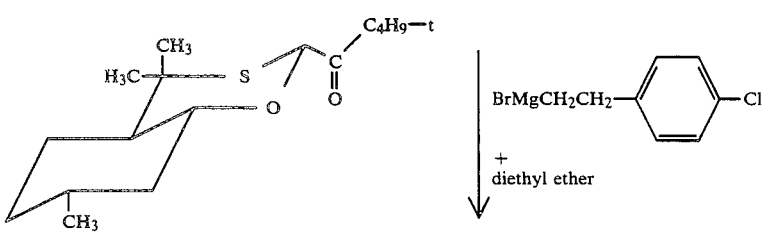

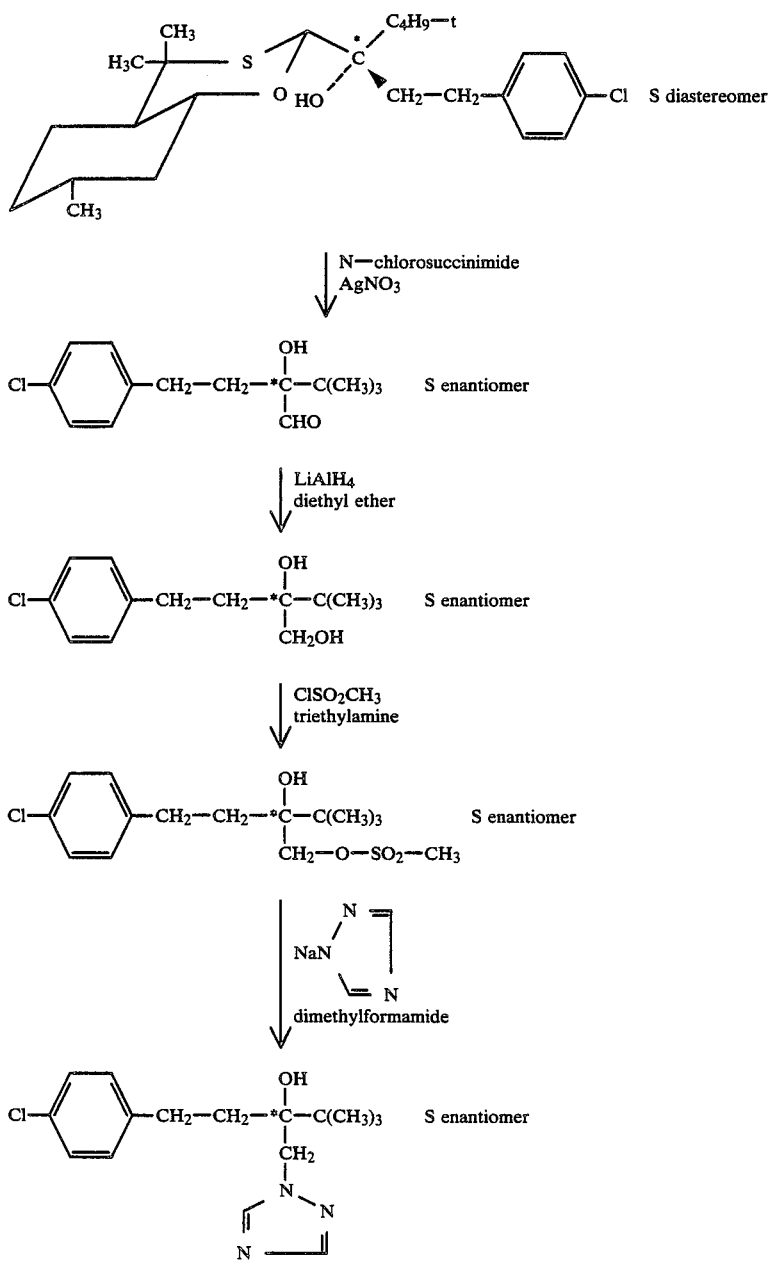

If, when carrying out version (c) of the process according to the invention, the 2-(4-chlorophenyl)-ethyl ketone which is derived from the enantiomerically-pure oxathiane of the formula (III-1) and tert.-butylmagnesium bromide are used as starting materials, N-chlorosuccinimide and silver nitrate are used as the reagent for the cleavage of the R diastereomer, produced virtually exclusively, in the second stage and lithium aluminium hydride is used for the reduction of the aldehyde in the second stage, chloromethanesulphonic acid is used as a reaction component in the third stage, and the sodium salt of triazole is used as a reactant in the fourth stage, the course of the process according to the invention may be illustrated by the following equation:

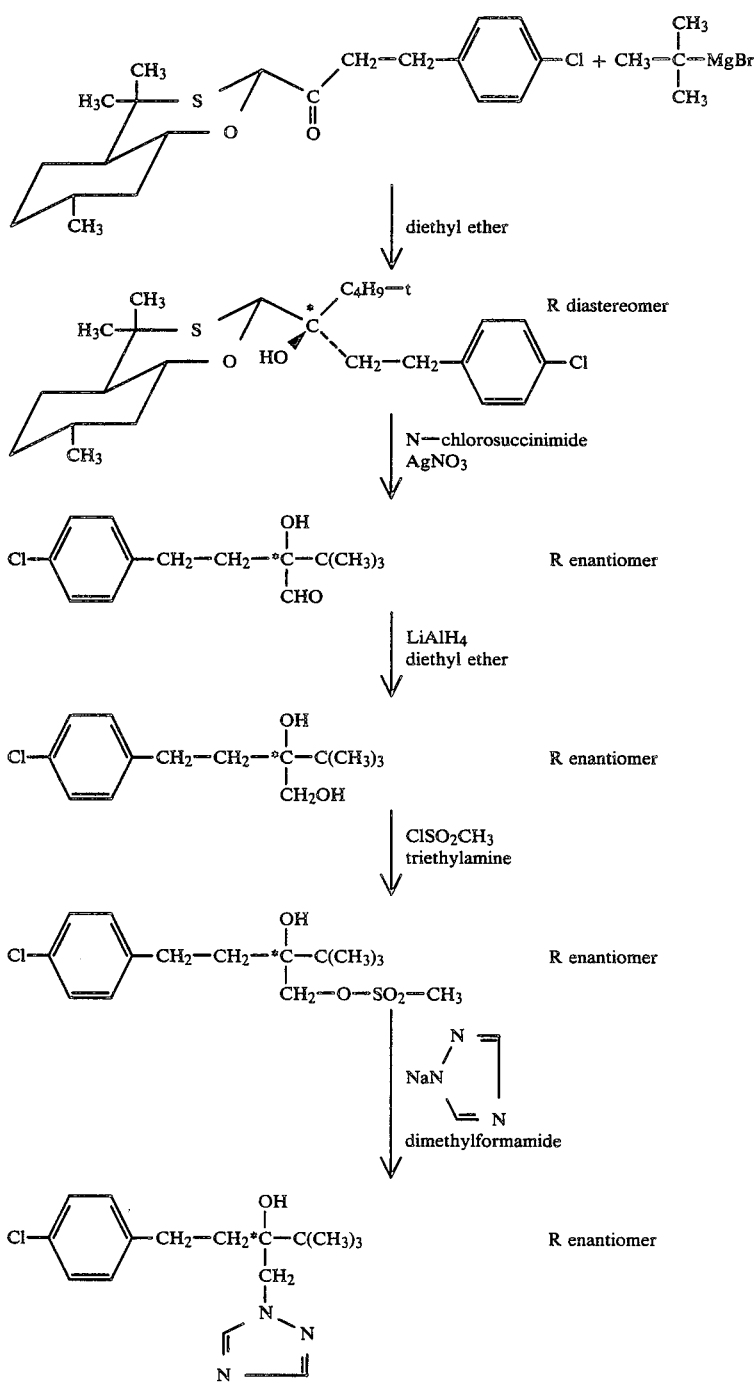

In the formula drawings above and in the part of the description which follows, the configuration arrangement "R" or "S" in each case refers to the carbinol carbon atom.

A general definition of the ketones which are required as starting materials when carrying out the process according to the invention according to version (a) is provided by the formula (II). Preferred substances of the formula (II) are those in which R represents straight-chain or branched alkyl, having 1 to 6 carbon atoms, which is optionally substituted by halogen, alkoxy having 1 to 4 carbon atoms, alkylthio having 1 to 4 carbon atoms, the formyl group and derivatives thereof, phenoxy and/or phenyl, alkyl having 1 to 4 carbon atoms, alkoxy having 1 to 4 carbon atoms, alkylthio having 1 to 4 carbon atoms and/or halogen-substituted cycloalkyl having 3 to 8 carbon atoms, or phenyl which is optionally substituted by alkyl having 1 to 4 carbon atoms, alkoxy having 1 to 4 carbon atoms, alkylthio having 1 to 4 carbon atoms and/or halogen, Y represents the —$CH_2$—$CH_2$—, —CH=CH— or —C≡C— groups or represents a direct bond, Z represents fluorine, chlorine, bromine, alkyl having 1 to 4 carbon atoms, cycloalkyl having 3 to 8 carbon atoms, alkoxy having 1 to 4 carbon atoms, alkylthio having 1 to 4 carbon atoms, halogenalkyl having 1 or 2 carbon atoms and 1 to 5 identical or different halogen atoms, halogenalkoxy having 1 or 2 carbon atoms and 1 to 5 identical or different halogen atoms, halogenalkythio having 1 or 2 carbon atoms and 1 to 5 identical or different halogen atoms, phenyl which is optionally substituted by halogen and/or alkyl having 1 to 4 carbon atoms, phenoxy which is optionally substituted by halogen and/or alkyl having 1 to 4 carbon atoms, phenylalkyl, having 1 or 2 carbon atoms in the alkyl part, which is optionally substituted by halogen and/or alkyl having 1 to 4 carbon atoms, or phenylalkoxy, having 1 or 2 carbon atoms in the alkoxy part, which is optionally substituted by halogen and/or alkyl having 1 to 4 carbon atoms, and m represents the numbers 0, 1, 2 or 3.

Particularly preferred compounds of the formula (II) are those in which

R represents alkyl, having 1 to 4 carbon atoms, which is optionally substituted by fluorine, chlorine, bromine, alkoxy having 1 or 2 carbon atoms, alkylthio having 1 to 2 carbon atoms, dioxolanyl, formyl, methoximinomethyl, phenoxy and/or phenyl, cycloalkyl, having 3 to 7 carbon atoms, which is optionally substituted by alkyl having 1 or 2 carbon atoms, alkoxy having 1 or 2 carbon atoms, alkylthio having 1 or 2 carbon atoms, fluorine, chlorine and/or bromine, or phenyl which is optionally substituted by alkyl having 1 or 2 carbon atoms, alkoxy having 1 or 2 carbon atoms, alkylthio having 1 or 2 carbon atoms, fluorine, chlorine and/or bromine.

Y represents the —$CH_2$—$CH_2$—, —CH=CH— or —C≡C— groups, or represents a direct bond, Z represents fluorine, chlorine, bromine, alkyl having 1 to 4 carbon atoms, cycloalkyl having 3 to 7 carbon atoms, alkoxy having 1 or 2 carbon atoms, alkylthio having 1 or 2 carbon atoms, halogenomethyl having 1 to 3 identical or different halogen atoms, halogenomethoxy having 1 to 3 identical or different halogen atoms, halogenomethylthio having 1 to 3 identical or different halogen atoms, phenyl which is optionally substituted by fluorine, chlorine and/or methyl, phenoxy which is optionally substituted by fluorine, chlorine and/or methyl, benzyl which is optionally substituted by fluorine, chlorine and/or methyl, or benzyloxy which is optionally substituted by fluorine, chlorine and/or methyl, and m represents the numbers 0, 1, 2, or 3.

Very particularly preferred substances of the formula (II) are those in which

R represents methyl, ethyl, isopropyl or tert.-butyl which is in each case optionally monosubstituted or disubstituted by fluorine, chlorine, bromine, methoxy, methylthio, methoximinomethyl, phenoxy and/or phenyl, the substituents being identical or different, or represents the grouping

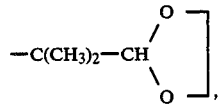

furthermore represents cyclopropyl, cyclopentyl or cyclohexyl which is in each case optionally monosubstituted or disubstituted by methyl, methylthio, fluorine and/or chlorine, the substituents being identical or different, or represents phenyl which is optionally monosubstituted or disubstituted by methyl, methoxy, methylthio, fluorine and/or chlorine, the substituents being identical or different, Y represents the —$CH_2$—$CH_2$—, —CH=CH—, or —C≡C— groups, or represents a direct bond, Z represents fluorine, chlorine, bromine, methyl, ethyl, isopropyl, tert.-butyl, cyclopropyl, cyclopentyl, cyclohexyl, methoxy, methylthio, trifluoromethyl, trifluoromethoxy, trifluoromethylthio, phenyl which is optionally monosubstituted or disubstituted by fluorine, chlorine and/or methyl, the substituents being identical or different, phenoxy which is optionally monosubstituted or disubstituted by fluorine, chlorine and/or methyl, the substituents being identical or different, benzyl which is optionally monosubstituted or disubstituted by fluorine, chlorine and/or methyl, the substituents being identical or different, or benzyloxy which is optionally monosubstituted or disubstituted by fluorine, chlorine and/or methyl, the substituents being identical or different, and m represents the numbers 0, 1, 2 or 3.

The ketones of the formula (II) are known or can be prepared in a simple fashion by methods which are known in principle (cf. German Patent Specification No. 2,201,063, DE-OS (German Published Specification) No. 2,705,678, DE-OS (German Published Specification) No. 2,737,489, EP-OS (European Published Specification) No. 0,111,711, Tetrahedron 31, 3 (1975) and Chemical Abstracts 84, 73 906 n).

The formula (III) provides a general definition of the enantiomerically-pure oxathianes which are furthermore required as starting materials for carrying out version (a) of the process according to the invention. Preferred oxathianes of the formula (III) are those in which $R^1$, $R^2$, $R^3$, $R^4$, $R^5$ and $R^6$ represent hydrogen or alkyl having 1 to 4 carbon atoms, but where at least one of these radicals represents alkyl having 1 to 4 carbon atoms and, in addition, $R^4$ and $R^5$, together, alternatively represent alkanediyl, having 3 to 6 cargon atoms which is optionally mono- to trisubstituted by alkyl having 1 to 4 carbon atoms, the substituents being identical or different, or, alternatively, $R^4$ and $R^5$, together with the neighbouring carbon atoms, represent a fused bicyclic hydrocarbon, having 7 or 8 carbon atoms, which is optionally mono- or trisubstituted by alkyl having 1 to 4 carbon atoms, the substituents being identical or different.

Particularly preferred oxathianes of the formula (III) are those in which $R^1$, $R^2$, $R^3$, $R^4$, $R^5$ and $R^6$ represent hydrogen, methyl or ethyl, but where at least one of these radicals represents methyl or ethyl and, in addition, $R^4$ and $R^5$, together, alternatively represent alkanediyl, having 3 to 5 carbon atoms, which is optionally mono- to trisubstituted by methyl and/or ethyl, the substituents being identical or different, or, alternatively, $R^4$ and $R^5$, together with the neighbouring carbon atoms, represent a fused bicyclic hydrocarbon, having 7 or 8 carbon atoms, which is optionally mon- to trisubstituted by methyl and/or ethyl, the substituents being identical or different.

The compounds of the following formulae may be mentioned as examples of enantiomerically-pure oxathianes of the formula (III):

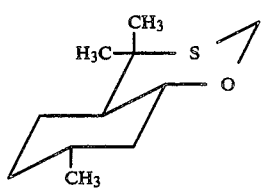
(III-1)

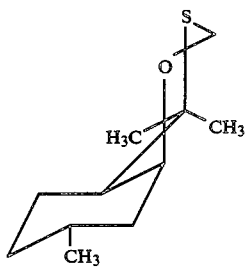
(III-2)

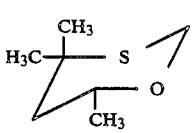
(III-3)

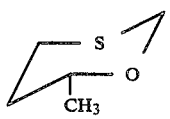
(III-4)

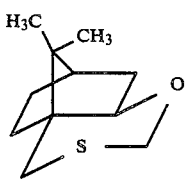
(III-5)

The enantiomerically-pure oxathianes of the formula (III) are known or can be prepared by processes which are known in principle (cf. Phosphorus Sulfur 24 (1985) 453–475, Asymmetric Synthesis Vol. 2 (1983) 125–155 and Asymmetric Reactions and Processes in Chemistry, ACS Symposium Series No. 185 (1982) 37–53).

Suitable strongly basic organometallic compounds when carrying out the first stage of version (a) of the process according to the invention are all compounds of this type which are suitable for such reactions. Alkyllithium compounds, such as n-butyl-lithium, furthermore phenyl-lithium and, in addition, lithium amides such as lithium di-isopropylamide, may preferably be used.

Suitable diluents when carrying out the first stage of version (a) of the process according to the invention are all organic solvents which are conventional for such reactions. Ethers, such as diethyl ether, tetrahydrofuran and dioxane, if appropriate with addition of polar solvents, such as hexamethyl-phosphoric triamide and tetramethyl-ethylenediamine, may preferably be used.

The reaction temperatures may be varied within a certain range when carrying out the first stage of version (a) of the process according to the invention. In general, the reaction is carried out at temperatures between $-80°$ C. and $+120°$ C., preferably between $-80°$ C. and $+100°$ C.

The first stage of version (a) of the process according to the invention is preferably carried out under a protective gas atmosphere, such as, for example, under nitrogen or argon. The reaction components of the formulae (II) and (III) are generally employed in equivalent amounts. However, it is also possible to employ an excess of one or other component. The work-up is effected by conventional methods. In general, a procedure is followed in which the reaction mixture is treated with aqueous ammonium chloride solution and extracted repeatedly with a sparingly water-soluble solvent, and the combined organic phases are dried and concentrated.

The diastereomeric compounds are separated in the second stage of version (a) of the process according to the invention by methods which are suitable for such purposes, thus, for example, by fractional crystallization or with the aid of chromatographic processes. In general, a procedure is followed in which the product obtained in the first stage is chromatographed, without prior purification, over a column. Silica gel is preferably suitable here as the stationary phase. Mixtures of nonpolar organic solvents, such as mixtures of hydrocarbons and ethers, are preferably used as the liquid phase. Examples which may be mentioned are mixtures of petroleum ether and diethyl ether.

The diastereomeric compounds can be separated in a simple fashion when carrying out the second stage of version (a) of the process according to the invention as a result of the different $R_f$-values. The compounds of the formula (IV-a) or (IV-b) are isolated by concentrating the respective eluate.

When carrying out the third stage of version (a) of the process according to the invention, a suitable material for cleaving the oxathiane compounds are all substances which are conventional for such purposes. Mixtures of N-chloro-succinimide and silver nitrate may preferably be used.

Suitable diluents for carrying out the cleavage of the oxathiane compounds are all solvents which are conventional for such reactions. Mixtures of water and polar organic diluents which are miscible with water may preferably be used. Examples which may be mentioned are mixtures of acetonitrile and water.

When carrying out the cleavage of the oxathiane compounds, all acid acceptors which are conventional for such reactions may be employed as acid-binding agents. Alkali metal carbonates and alkali hydrogen carbonates, such as, for example sodium hydrogen carbonate, may preferably be used.

The reaction temperatures may be varied within a relatively wide range when carrying out the cleavage of the oxathiane compounds in the third stage of version (a) of the process according to the invention. In general, the reaction is carried out at temperatures between 0° C. and 100° C., preferably between 20° C. and 60° C.

When carrying out the cleavage of the oxathiane compounds, 1 to 3 moles of cleavage reagent and an excess of acid-binding agent are generally employed per mole of the diastereomeric compound of the formula (IV-a) or (IV-b). The work-up is effected by conventional methods. In general, a procedure is followed in which the reaction mixture is treated with aqueous salt solutions, the solid components are filtered off, the filtrate is extracted repeatedly with sparingly water-soluble organic solvents, and the combined organic phases are washed, dried and concentrated. The product produced may be used for the further reactions without additional purification.

When carrying out version (a) of the process according to the invention, suitable reagents for the reduction of optically active α-hydroxyaldehydes of the formula (V) are preferably complex hydrides, such as lithium aluminium hydride and sodium borohydride.

Suitable diluents for the reduction of optically active α-hydroxyaldehydes of the formula (V) are all inert organic solvents. Ethers, such as diethyl ether or tetrahydrofuran, may preferably be used. If sodium borohydride is used as reducing agent, then it is also possible to employ alcohols, such as methanol or ethanol, or nitriles, such as acetonitrile, if appropriate as a mixture with water, as diluents.

The reaction temperatures may be varied within a certain range when carrying out the reduction in the third stage of version (a) of the process according to the invention. In general, the reaction is carried out at temperatures between $-20°$ C. and $+100°$ C., preferably between 20° C. and 60° C.

When carrying out the reduction in the third stage of version (a) of the process according to the invention, 1 to 5 moles of reducing agent are generally employed per mole of optically active α-hydroxyaldehyde of the formula (V). The work-up is effected by conventinal methods. In general, a procedure is followed in which the reaction mixture is treated with a sparingly water-soluble organic solvent and with an aqueous alkali metal hydroxide solution, the solid components which are present are filtered off, and the organic phase, after drying, is concentrated. However, it is also possible to initially concentrate the reaction mixture when the reaction is complete, to extract the product remaining using a sparingly water-soluble organic solvent, and to dry and subsequently to concentrate the combined organic phases. The product produced can, if appropriate after prior purification, be used for the further reactions.

The formula (VII) provides a general definition of the sulphonic acid derivatives which are required as reaction components when carrying out the fourth stage of version (a) of the process according to the invention. Sulphonic acid derivatives of the formula (VII) in which $R^7$ represents alkyl having 1 to 4 carbon atoms, halogenoalkyl having 1 or 2 carbon atoms and 1 to 5 halogen atoms, or optionally methyl-substituted phenyl, and Hal represents chlorine or bromine, may preferably be used.

The following may be mentioned as examples of sulphonic acid derivatives of the formula (VII): methanesulphonyl chloride, ethanesulphonyl chloride, trifluoromethane-sulphonyl chloride and p-tolylsulphonyl chloride.

The sulphonic acid derivatives of the formula (VII) are generally known compounds of organic chemistry.

Suitable acid-binding agents when carrying out the fourth stage of version (a) of the process according to the invntion are preferably lower tertiary alkylamines, cycloalkylamines, aralkylamines or arylamines. Examples which may be mentioned are triethylamine, N,N-dimethylbenzylamine, pyridine, 1,4-diazabicyclo[2,2,-2]octane and 1,5-diazabicyclo[4,3,0]non-5-ene.

Suitable diluents when carrying out the fourth stage of version (a) of the process according to the invention are all organic solvents which are conventional for such reactions. Halogenated hydrocarbons, such as methylenechloride, chloroform and carbon tetrachloride, may preferably be used.

The reaction temperatures may be varied within a certain range when carrying out the fourth stage of version (a) of the process according to the invention. In general, the reaction is carried out at temperatures between 0° C. and 100° C., preferably between 0° C. and 50° C.

When carrying out the fourth stage of version (a) of the process according to the invention, 1 to 1.3 moles of sulphonic acid derivative of the formula (VII) and 1 to 1.3 moles of acid-binding agent are generally employed per mole of optionally active diol of the formula (VI). The work-up is effected by conventional methods. In general, a procedure is followed in which the reaction mixture is initially washed with weakly acidic aqueous solution and then with weakly basic aqueous solution, then dried and concentrated. The product produced may be used for the further reaction without additional purification.

The triazole salts which are required as reaction components for carrying out the fifth stage of version (a) of the process according to the invention are defined by the formula (IX). Preferred substances are those in which Me represents sodium or potassium.

The triazole salts of the formula (IX) are known.

All conventional organic and inorganic bases may be employed as acid-binding agents when carrying out the fifth stage of version (a) of the process according to the invention. Alkali metal carbonates, such as, for example, sodium carbonate or sodium hydrogen carbonate, furthermore lower tertiary alkylamines, cycloalkylamines, arylalkylamines or arylamines, such as, for example, triethylamine, N,N-dimethylbenzylamine, pyridine, 1,4-diazabicyclo[2,2,2]-octane or 1,5-diazabicyclo-[4,3,0]-non-5-ene, may preferably be used.

Suitable diluents for carrying out the fifth stage of version (a) of the process according to the invention are all inert organic solvents which are conventional for such reactions. Polar, aprotic diluents, such as dimethylformamide and dimethyl solphoxide, may preferably be used.

The reaction temperatures may be varied within a relatively wide range when carrying out the fifth stage of version (a) of the process according to the invention. In general, the reaction is carried out at temperatures between 20° C. and 150° C., preferably between 50° C. and 150° C.

The reactions in the fifth stage of version (a) of the process according to the invention are preferably carried out under a protective gas atmosphere, such as, for example, under nitrogen or argon.

When carrying out the fifth stage of version (a) of the process according to the invention, 2 to 4 moles of triazole salt of the formula (IX) are generally employed per mole of optically active compound of the formula (VIII). The work-up is effected by conventional methods. In general a procedure is followed with the reaction mixture, if appropriate after prior stripping off of the diluent, is treated with water and with a sparingly water-soluble organic solvent, the organic phase is separated off, dried and concentrated, and the residue remaining is purified by a chromatographic route.

The formula (X) provides a general definition of the oxathiane ketones which are required as starting materials when carrying out the first stage of version (b) of the process according to the invention. In this formula, R, $R^1$, $R^2$, $R^3$, $R^4$, $R^5$ and $R^6$ preferably have the meanings which have already been mentioned in connection with the description of the compounds of the formulae (II) and (III) as being preferred for these radicals.

Some of the oxathiane ketones of the formula (X) are known. They can be prepared by reacting enantiomerically-pure oxathianes of the formula

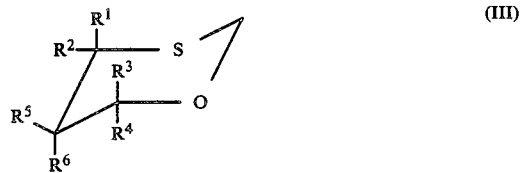
(III)

in which
 $R^1$, $R^2$, $R^3$, $R^4$, $R^5$ and $R^6$ have the abovementioned meaning,
with aldehydes of the formula

R—CHO    (XIV)

in which
R has the abovementioned meaning,
in the presence of a strongly basic organometallic compound, such as n-butyl-lithium or phenyllithium, in the presence of a diluent, such as diethyl ether or tetrahydrofuran, under a protective gas atmosphere at temperatures between $-80°$ C. and $+120°$ C., and oxidizing the carbinols of the formula

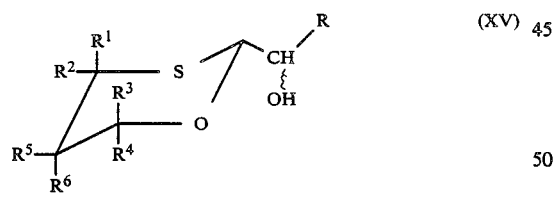
(XV)

in which
R, $R^1$, $R^2$, $R^3$, $R^4$, $R^5$ and $R^6$ have the abovementioned meaning.

The preferred oxidation process comprises reacting with dimethyl sulphoxide in the presence of trifluoroacetic anhydride and triethylamine and in the presence of an additional diluent, such as methylene chloride, at temperatures between $-80°$ C. and $+50°$ C.

The formula (XI) provides a general definition of the organometallic compounds which are required as reaction components in the first stage when carrying out version (b) of the process according to the invention. Preferred compounds of the formula (XI) are those in which
 Y, Z and m have the meanings which have already been mentioned in connection with the description of the ketones of the formula (II) as being preferred for these radicals, and
 $R^8$ represents lithium, sodium, potassium, titanium alcoholates, such as titanium isopropylate, or a radical of the formula $Me^1X$, in which $Me^1$ represents magnesium or zinc and X represents chlorine, bromine or iodine.

The organometallic compounds of the formula (XI) are known or can be prepared by processes which are known in principle.

Suitable diluents for carrying out the first stage of version (b) of the process according to the invention are all organic solvents which are conventional for such reactions. Ethers, such as diethyl ether, tetrahydrofuran and dioxane, may preferably be used.

The reaction temperatures may be varied within a certain range when carrying out the first stage of version (b) of the process according to the invention. In general, the reaction is carried out at temperatures between $-78°$ C. and $+100°$ C., preferably between $-78°$ C. and $+90°$ C.

When carrying out the first stage of version (b) of the process according to the invention, 1 to 2 moles of organometallic compound of the formula (XI) are generally employed per mole of oxathiane ketone of the formula (X). The work-up is effected by conventional methods. In general, a procedure is followed in which the reaction mixture is treated with aqueous ammonium chloride solution, the organic phase is separated off, the aqueous phase is extracted repeatedly with a sparingly water-miscible organic solvent, and the combined organic phases are dried, concentrated and incipiently distilled under reduced pressure. Any further purification which may be necessary can be carried out by conventional methods.

The product obtained in the first stage of version (b) of the process according to the invention consists to more than 95% of one of the two possible diastereomers of the formula (IV). In general, it is not necessary to separate off the diastereomer which is present in a low amount before the further reaction. However, the separation can be carried out in a simple fashion. A procedure is followed here as has been described for the second stage of version (a) of the process according to the invention.

Suitable materials for the cleavage of the oxathiane compounds when carrying out the third stage of version (b) of the process according to the invention are all substances which are conventional for such purposes. Mixtures of N-chloro-succinimide and silver nitrate may preferably be used.

In addition, the reaction conditions when carrying out the second stage of version (b) of the process according to the invention correspond to those which are used in the third stage of version (a) of the process according to the invention. The further reactions when carrying out version (b) of the process according to the invention are also carried out in the fashion which has been described in connection with version (a).

The formula (XII) provides a general definition of the oxathiane ketones which are required as starting materials for carrying out version (c) of the process according to the invention. In this formula, $R^1$, $R^2$, $R^3$, $R^4$, $R^5$, $R^6$, Y, Z and m preferably having the meanings which have already been mentioned in connection with the description of the compounds of the formulae (II) and (III) as being preferred for these radicals and the index m.

The oxathiane ketones of the formula (XII) can be prepared by reacting enantiomerically-pure oxathianes of the formula

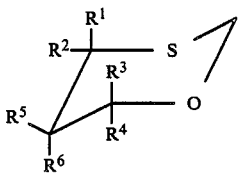
(III)

in which
R$^1$, R$^2$, R$^3$, R$^4$, R$^5$ and R$^6$ have the abovementioned meaning,
with aldehydes of the formula

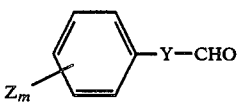
(XVI)

in which
Y, Z and m have the abovementioned meaning,
in the presence of a strongly basic organometallic compound, such as n-butyl-lithium or phenyllithium, in the presence of a diluent, such as diethyl ether or tetrahydrofuran, under a protective gas atmosphere at temperatures between $-80°$ C. and $+120°$ C., and the resultant carbinoles of the formula

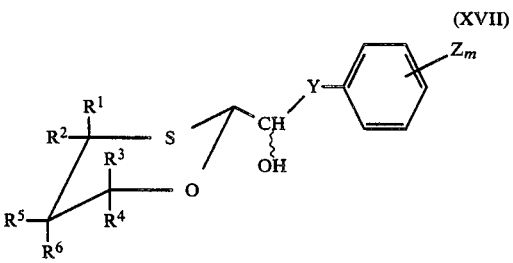
(XVII)

in which
R$^1$, R$^2$, R$^3$, R$^4$, R$^5$, R$^6$, Y, Z and m have the abovementioned meaning,
are reacted with dimethyl sulphoxide in the presence of trifluoroacetic anhydride and triethylamine and in the presence of an additional diluent, such as methylene chloride at temperatures between $-80°$ C. and $+50°$ C.

The formula (XIII) provides a general definition of the organometallic compounds which are required as reaction components in the first stage when carrying out version (c) of the process according to the invention. Preferred compounds of the formula (XIII) are those in which R and R$^8$ have the meanings which have already been mentioned in connection with the description of the compounds of the formulae (II) and (XI) as being preferred for these radicals.

The organometallic compounds of the formula (XIII) are known or can be prepared by processes which are known in principle.

Suitable diluents for carrying out the first stage of version (c) of the process according to the invention are all organic solvents which are conventional for such reactions. Ethers, such as diethyl ether, tetrahydrofuran and dioxane, may preferably be used.

The reaction temperatures may be varied within a certain range when carrying out the first stage of version (c) of the process according to the invention. In general, the reaction is carried out at temperatures between $-78°$ C. and $+100°$ C., preferably between $-78°$ C. and $+90°$ C.

When carrying out the first stage of version (c) of the process according to the invention, 1 to 2 moles of organometallic compound of the formula (XIII) are generally employed per mole of oxathiane ketone of the formula (XII). The work-up is effected by conventional methods. In general, a procedure is followed in which the reaction mixture is treated with aqueous ammonium chloride solution, the organic phase is separated off, the aqueous phase is extracted repeatedly with a sparingly water-miscible organic solvent, and the combined organic phases are dried, concentrated and incipiently distilled under reduced pressure. Any further purification which may be necessary can be carried out by conventional methods.

The product obtained in the first stage of version (c) of the process according to the invention consists to more than 95% of one of the two possible diastereomers of the formula (IV). In general, it is not necessary to separate off the diastereomer present in a low amount before the further reaction. However, the separation can be carried out in a simple fashion by a chromatographic route. A procedure is followed here as has been described for the second stage of version (a) of the process according to the invention.

Suitable materials for the cleavage of the oxathiane compounds when carrying out the third stage of version (c) of the process according to the invention are all substances which are conventional for such purposes. Mixtures of N-chloro-succinimide and silver nitrate may preferably be used.

In addition, the reaction conditions when carrying out the second stage of version (c) of the process according to the invention correspond to those which are used in the third stage of version (a) of the process according to the invention. The further reactions when carrying out version (c) of the process according to the invention are also carried out in the fashion which has been described in connection with version (a).

Version (a) of the process according to the invention is suitable both for the preparation of those optically active 2-hydroxyethyl-azole derivatives of the formula (I) which have the R configuration at the asymmetrically substituted carbon atom and for the synthesis of the corresponding S enantiomers. Versions (b) and (c) are particularly suitable for the preparation of either the R enantiomer or the S enantiomer. If the R enantiomer is obtained in the synthesis of a certain compound by version (b), the corresponding S enantiomer is produced in the preparation of the same compound by version (c). The enantiomers of the 2-hydroxyethyl-azole derivatives of the formula (I) which are desired in each case may thus be prepared specifically with the aid of the process according to the invention.

The optically active 2-hydroxyethyl-azole derivatives of the formula

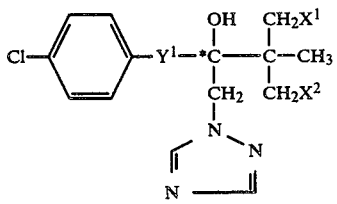

(Ia)

in which
X¹ represents hydrogen, fluorine or chlorine,
X² represents hydrogen, fluorine or chlorine, and
Y¹ represents the —CH₂—CH₂—, —CH=CH— or —C≡C— groups, are new.

The optically active 2-hydroxyethyl-azole derivatives of the formula (I) which may be prepared by the process according to the invention are distinguished by excellent fungicidal and plant growth-regulating properties. In each case they surpass the corresponding racemates in their action.

The active compounds which may be prepared according to the invention have a strong microbicidal action and may be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, *Xanthomonas oryzae;* Pseudomonas species, such as, for example, *Pseudomonas lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminae* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerae;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds which can be prepared according to the invention, at the concentrations required for combating plant diseases, permits treatment of above-ground parts of plants, of vegetative propagation stock and seeds, and of the soil.

In addition, the active compounds which can be prepared according to the invention also have plant growth-regulating properties.

The active compounds which can be prepared according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants a verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds which can be prepared according to the invention can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysation products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds which can be prepared according to the invention can be present in the formulations as a mixture with other known active compounds, such as fungicides, insecticides, acaricides and herbicides, and also as mixtures with fertilisers and other growth regulators.

The active compounds which can be prepared according to the invention can be used as such, in the form of their formulations or in the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomising, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the substances which can be prepared according to the invention are employed as fungicides, the amount applied may be varied within a relatively wide range according to the type of application. Thus, in the treatment of parts of plants, the active compound concentrations in the forms of application are generally between 1 and 0.0001% by weight, preferably between 0.5 and 0.001%. In the treatment of seed, active compound amounts from 0.001 to 50 g per kilogramme of seed, preferably 0.01 to 10 g, are generally required. In the treatment of soil, active compound concentrations from 0.00001 to 0.1% by weight, preferably from 0.0001 to 0.02%, are required at the place of action.

When the compounds which can be prepared according to the invention are employed as plant growth regulators, the amounts applied may be varied within a relatively wide range. In general, 0.01 to 50 kg, preferably 0.05 to 10 g, of active compound are used per hectare of soil surface.

When the substances which can be prepared according to the invention are employed as plant growth regulators, the rule is that the growth regulators are applied within a preferred period of time, the exact definition of which depends on the climatic and vegetative circumstances.

The execution of the process according to the invention is illustrated by the following examples.

EXAMPLE 1

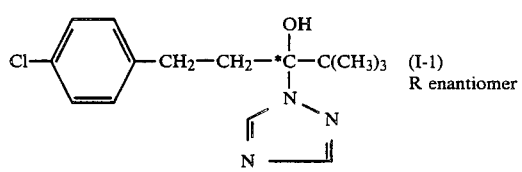

Process version (a)

1st stage

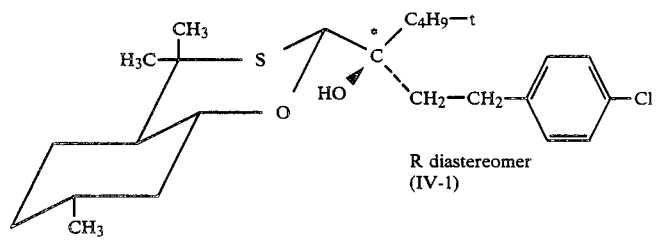

R diastereomer
(IV-1)

and

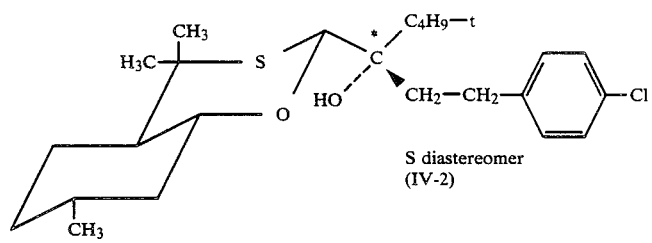

S diastereomer
(IV-2)

45.5 ml (90 mmol) of n-butyl-lithium in n-hexane (;b 1.98 molar) are added to a solution of 18.0 g (90 mmol) of oxathiane compound of the formula

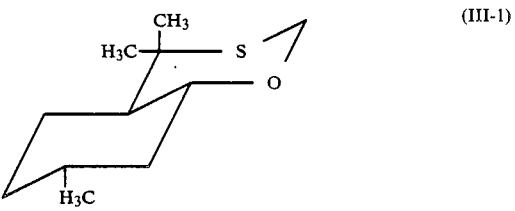

in 150 ml of absolute tetrahydrofuran at −78° C. under a nitrogen atmosphere. The solution is warmed briefly to 0° C., then recooled to −78° C., a solution of 20.2 g (90 mmol) of 2,2-dimethyl-5-(4-chlorophenyl)-pentan-3-one in 50 ml of absolute tetrahydrofuran is added dropwise with stirring at this temperature, and the reaction mixture is then warmed slowly to room temperature and stirred for a further 30 minutes at 25° C. For work-up, the reaction mixture is poured into 150 ml of saturated, aqueous ammonium chloride solution and extracted three times with methylene chloride. The combined organic phases are dried over sodium sulphate and subsequently concentrated under reduced pressure. In this fashion, 37.6 g of a product which consists to 98% of the diastereomers of the formulae (IV-1) and (IV-2), are obtained, the R diastereomer of the formula (IV-1) being present to 74% and the S diastereomer of the formula (IV-2) being present to 26% in the mixture of diastereomers according to gas-chromatographic analysis.

R$_F$ values (silica gel; petroleum ether: diethyl ether=5:1)
R diastereomer: R$_F$=0.43.
S diastereomer: R$_F$=0.31.

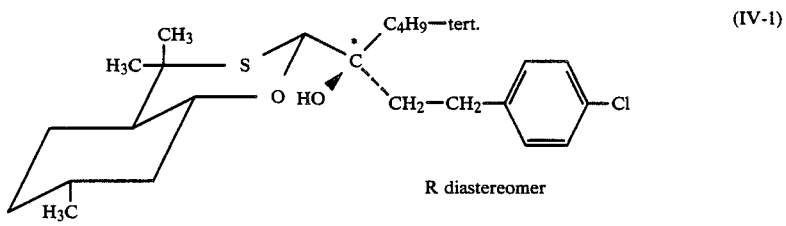

R diastereomer

In each case, 13 g of the mixture of diastereomers obtained in the first stage are chromatographed over a column of silica gel, a mixture of petroleum ether:-diethyl ether=5:1 being employed as eluate. After concentration of the eluted fractions,
20.5 g (54% of theory) of the R diastereomer of the formula (IV-1)
and
7.04 g (18% of theory) of the S diastereomer of the formula (IV-2)
are obtained.

The substances are present in the form of colourless oils.

According to the gas-chromatographic analysis, the R diastereomer is completely diastereomerically pure, whereas the S diastereomer still contains 2–3% of R diastereomer.

IR spectrum (NaCl):
Identical for the R diastereomer and the S diastereomer; in each case OH bands at 3,550 cm$^{-1}$.

Mass spectrum
Identical for the R diastereomer and the S diastereomer m/e=424 (M$^+$, not present); 367 (4%, M$^+$-tert.-butyl); 199 (100%, oxathiane fragment).

$^1$H NMR spectrum (360 MHz, CDCl$_3$):
R diastereomer:
σ=0.92 (d, 3HCH$_3$—CH) 1.03 (s, 9H, tert.-butyl) 1.29 and 1.44 (each s, each 3H, CH$_3$—C—CH$_3$) 2.59 and 3.09 (each d of t, J=5.0; 13.1 Hz, each 1H,

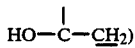

3.37 (s, 1H, OH) 3.41 L (d of t, 1H, —CH—O) 5.05 (s, 1H,

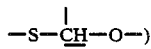

7.17–7.30 (m, 4H, arom. H).

S diastereomer:
σ=0.93 (α, 3H, CH$_3$—CH) 1.02 (s, 9H, tert.-butyl) 1.29 and 1.42 (each s, each 3H, CH$_3$—C—CH$_3$) 2.75 L and 30.5 (each d of t, J=4.9; 12.8 Hz, each 1H,

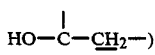

2.06 (s, 1H, OH) 3.36 (d of t, 1H, —CH—O—) 5.29 (s, 1H,

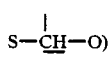

7.15–7.28 (m, 4H, arom. H).

3rd stage

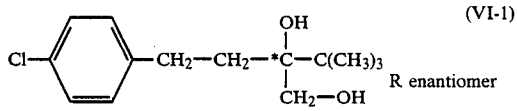

R enantiomer

A solution of 17.9 g (42 mmol) of the R diasteromer of the formula (IV-1) in 75 L ml of acetonitrile is added, with stirring, to a mixture, warmed to 40°–50° C., of 13.5 g (101 mmol) of N-chloro-succinimide, 14.3 g (84 L mmol) of silver nitrate, 11.3 g (134 mmol) of sodium hydrogen carbonate, 250 ml of acetonitrile and 50 ml of water. The mixture is stirred for a further 15 minutes at 40° to 50° C., 38 ml of saturated, aqueous sodium sulphite solution and 38 ml of saturated, aqueous sodium chloride solution are then successively added dropwise, the mixture is filtered off under suction and the residue is washed with a mixture of methylene chloride/hexane=1:1.

The filtrate is extracted twice with the same volume of a mixture of methylene chloride/hexane 1:1 in each case. The organic phase is separated off, washed with saturated, aqueous sodium hydrogen carbonate solution, dried over sodium sulphate, concentrated under reduced pressure, and subsequently freed in a high vacuum of the solvent residues still present. The product produced here, the major proportion of which is optically active α-hydroxyaldehyde of the formula

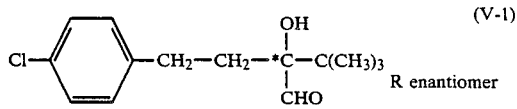

R enantiomer is dissolved in 75 ml of diethyl ether and added dropwise at room temperature with stirring to a suspension of 7.96 g (0.21 mol) of lithium aluminium hydride in 80 ml of absolute diethyl ether. That mixture is refluxed for 3 hours, 14 ml of ethyl acetate, 14 ml of 4N aqueous sodium hydroxide solution and 14 ml of water are then successively added dropwise, the mixture is filtered off under suction, washed with diethyl ether, and the organic phase is dried over sodium sulphate and concentrated under reduced pressure.

In this fashion, 11.8 g of a product which, according to gas-chromatographic analysis, consists to 80% of the optically active diol of the formula (IV-1), are obtained.

IR spectrum (NaCl): OH bands at 3,100–3,600 cm$^{-1}$.

Mass spectrum m/e=256 (M$^+$, not present); 199 (18%, M$^+$-tert.-butyl), 181 (37%, M$^+$-H$_2$O-tert.-butyl); 125 (100%,

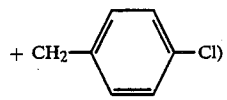

$^1$HNMR spectrum (360 MHz, CDCl$_3$): σ=0.97 (s, 94, tert.-butyl) 1.70–1.93 (m, 2H, C$\underline{H_2}$—Ph—Cl) 2.70–2.80 (m, 2H,

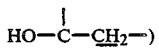

3.65 and 3.78 (dd, J=11.0 Hz, 2H, —C$\underline{H_2}$—OH) 7.13—7.35 (m, 4H, aromat. H).

The aluminum hydroxide precipitate produced during the reduction using lithium aluminium hydride is dissolved in 500 ml of 10% strength aqueous hydrocloric acid. The resultant solution is extracted four times with methylene chloride. The combined organic phases are dried over sodium sulphate and concentrated under reduced pressure. In this fashion, 5.02 g (64% of theory) of 1-hydroxy-2-(1-methyl-1-mercapto-ethyl)-5-methyl-cyclohexane are obtained in the form of a virtually enantiomerically-pure product.

4th stage

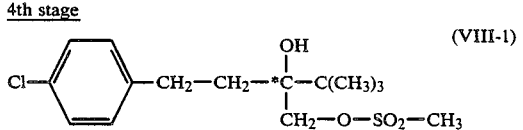

R enantiomer

A solution of 4.80 g (42 mmol) of methane sulphonyl chloride in 50 ml of absolute methylene chloride and a solution of 4.2 g (42 mmol) of triethylamine in 50 ml of absolute methylene chloride are simultaneously added dropwise at 0° C. with stirring to a solution of 10.78 g (42 mmol) of the R enantiomer of the formula (VI-1) in 100 ml of absolute methylene chloride under a nitrogen atmosphere. The mixture is stirred for a further 4 hours at 0° C. and then warmed to 25° C. The reaction mixture is extracted successively with saturated, aqueous citric acid solution and with saturated, aqueous sodium hydrogen carbonate solution, dried over sodium sulphate and concentrated under reduced pressure. In this fashion, 14.0 g of a product which consists to 80% of the R enantiomer of the formula (VII-1), are obtained. The yield accordingly works out at 80% theory.

The product is further reacted without additional purification.

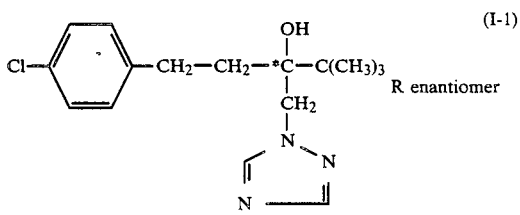

A mixture of 14.06 g (42 mmol) of the R enantiomer of the compound of the formula (VIII-1), 11.47 g (126 mmol) of the sodium salt of triazole and 50 liters of dimethylformamide is stirred for 6 hours at 120° C. under a nitrogen atmosphere. The mixture is then concentrated under reduced pressure and the residue remaining is added to a mixture of water and methylene chloride. The organic phase is separated off, the aqueous phase is extracted twice with methylene chloride, and the combined organic phases are dried over sodium sulphate and concentrated. 11.40 g of a product, which is purified by column chromatography on 350 g of silica gel using a mixture of methylene chloride/methanol=95:5 as eluate, remain. 5.56 g of a product, which consists, according to gas-chromatographic analysis, to 93–95% of the R enantiomer of 2,2-dimethyl-5-(4-chlorophenyl)-3-(1,2,4-triazole-1-yl-methyl)pentan-3ole, are obtained by concentrating the eluate. From this, the yield works out at 43% of theory, relative to the R diastereomer of the formula (IV-1).

[α]$_D^{20}$= +34.1° (c=1, CHCl$_3$).

Optical purity ≧84%.

Content of S enantiomer ≦8%.

Mass spectrum (ci): me=308 (100%, M$^+$ +H).

$^1$H NMR spectrum (360 MHz, CDCl$_3$): σ=1.04 (s, 9H, tert.-butyl) 1.70–2.00 (m, 2H,

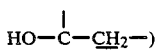

2.30–2.60 (m, 2H—C$\underline{H_2}$—Ph—Cl) 3.37 (s, 1H, —O$\underline{H}$) 4.35 (s, 2H, —C$\underline{H_2}$—triazole) 6.90–7.30 (m, 4H, aromat. H) 8.00 and 8.35 (each s, each 1H, triazole-H).

EXAMPLE 2

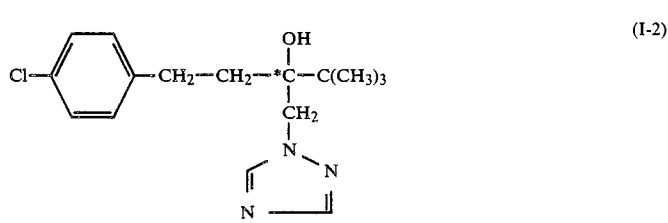

S enantiomer

Process version (b)
1st stage

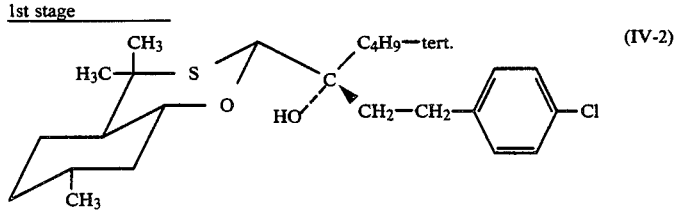

S diastereomer

A solution of 48.3 g (0.22 mol) of 2-(4-chlorophenyl)-ethyl bromide in 100 ml of absolute diethyl ether is added dropwise to a suspension of 5.30 g (0.22 mol) of magnesium turnings in 10 ml of absolute diethyl ether under a nitrogen atmosphere and with stirring at a rate such that the reaction mixture boils smoothly. The mixture is refluxed for 2 hours until all the magnesium has dissolved. The mixture is cooled to −78° C. and, at this temperature, a solution of 31.3 g (0.11 mol) of the oxoathiane ketone of the formula

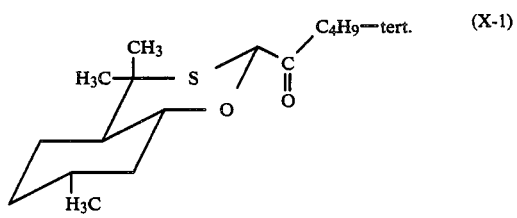

in 200 ml of absolute diethyl ether is added dropwise.

The mixture is then initially warmed slowly to room temperature and the refluxed for 3 hours. For work-up, the reaction mixture is poured into 200 ml of saturated, aqueous ammonium chloride solution, the organic phase is separated, the aqueous phase is extracted three times with methylene chloride, and the combined organic phases are dried over sodium sulphate and concentrated under reduced pressure. 116.8 g of a product, which consists to
47.6% of the S diastereomer of the formula (IV-2),
1.13% of the R diastereomer of the formula (IV-1),
30% of 4-chloro-ethylbenzene,
2% of 2-(4-chlorophenyl)-ethanol and
1% of di-(4-chlorophenyl)-butane,
remain as residue.

The S diasteromer of the formula (IV-2) and the R diastereomer of the formula (IV-1) are present in the ratio 97.7:2.3 (95.4% of theory).

The low-boiling components are removed by incipient distillation in a high vacuum at 140° C. 40.2 g of a product which consists to 80% of the S diastereomer of the formula (IV-2) are obtained. The product is reacted further without additional purification.

IR spectrum (NaCl): OH Bands at 3,550 cm⁻¹.

Mass spectrum: m/e=424 (M+, not present); 367 (4%, M*-tert.-butyl); 199 (100%, oxathiane fragment).

¹NMR spectrum (360 MHz, CDCl₃): σ=0.93 (d, 3H, CH₃—CH) 1.02 (s, 9H, tert.-butyl) 1.29 and 1.42 (each s, each 3H, CH₃—C—CH₃) 2.75 and 3.05 (each d of t, J=4.9; 12.8 Hz, each 1H,

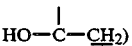

2.06 (s, 1H, OH) 3.36 (d of +, 1H,

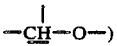

5.29 (s, 1H,

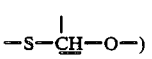

7.15–7.28 (m, 4H, arom. H).

2nd stage

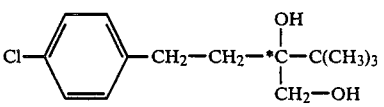

S enantiomer

A solution of 40.2 g (0.11 mol) of the S diastereomer of the formula (IV-2) in 150 ml of absolute acetonitrile is added with stirring to a mixture, warmed to 40°–50° C., of 35.2 g (0.26 mol) of N-chlorosuccinimide, 37.3 g (0.22 mmol) of silver nitrate, 29.5 g (0.35 mol) of sodium hydrogen carbonate, 500 ml of acetonitrile and 100 ml of water. The mixture is stirred for a further 15 minutes at 40° to 50° C., then 82 ml of saturated, aqueous sodium sulphite solution and 82 ml of saturated, aqueous sodium chloride solution are successively added dropwise, the mixture is filtered off under suction, and the residue is washed with a mixture of methylene chloride hexane=1:1.

The filtrate is extracted twice with the same volume of a mixture of methylene chloride/hexane=1:1 in each case. The organic phase is separated off, washed with saturated, aqueous sodium hydrogen carbonate solution, dried over sodium sulphate, concentrated under reduced pressure, and subsequently freed in a high vacuum of solvent residues which are still present. The product produced during this, the major proportion of which is optically active α-hydroxyaldehyde of the formula

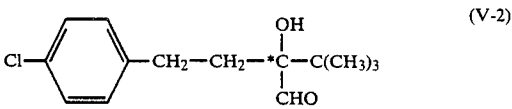

35
-continued

S enantiomer is dissolved in 100 ml of absolute diethyl ether and added dropwise at room temperature with stirring to a suspension of 20.8 g (0.55 mol) of lithium aluminium hydride in 150 ml of absolute diethyl ether. The reaction mixture is refluxed for 3 hours, 28 ml of ethyl acetate, 28 ml of 4N aqueous sodium hydroxide solution and 28 ml of water are then successively added dropwise, the mixture is filtered off under suction, washed with diethyl ether, and the organic phase is dried over sodium sulphate and concentrated under reduced pressure.

In this fashion, 24.1 g of a product which, according to gas-chromatographic analysis, consists to 80% of the optically active diol of the formula (VI-2) are obtained.

IR spectrum (NaCl): OH bands at 3,100–3,600 cm$^{-1}$.

Mass spectrum m/e=256 (M$^+$, not present); 199 (18%, M$^+$-tert.-butyl), 181 (37%, M$^+$—H$_2$O—tert.-butyl); 125 (100%,

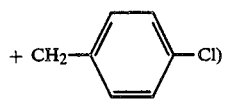

$^1$H NMR spectrum (360 MHz, CDCl$_3$) $\sigma$=0.97 (s, 94, tert.-butyl) 1.70–1.93 (m, 2H, —CH$_2$—Ph—Cl) 2.70–2.80 (m, 2H,

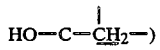

3.65 and 3.78 (dd, J=11.0 Hz, 2H, —CH$_2$OH) 7.13–7.35 (m, 4H, aromat. H).

The aluminium hydroxide precipitate produced during the reduction using lithium aluminium hydride is dissolved in 1 liter of 10% strength aqueous hydrochloric acid. The resultant solution is extracted four times with methylene chloride. The combined organic phases are dried over sodium sulphate and concentrated under reduced pressure. In this fashion, 12.2 g (59% of theory) of 1-hydroxy-2-(1-methyl-1-mercapto-ethyl)-5-methyl-cyclohexane are obtained in the form of a virtually enantiomerically-pure product.

3rd Stage

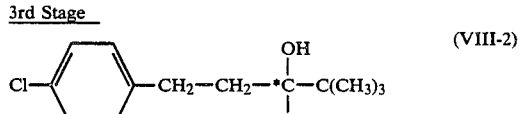

S enantiomer

A solution of 11.8 g (103 mmol) of methane sulphonyl chloride in 50 ml of absolute methylene chloride and a solution of 10.4 (103 mmol) of triethylamine in 50 ml of absolute methylene chloride are simultaneously added dropwise at 0° C. with stirring to a solution of 24.0 g (93.4 mmol) of the S enantiomer of the formula (VI-2) in 100 ml of absolute methylene chloride under a nitrogen atmosphere. The mixture is stirred for a further 4 hours at 0° C. and then warmed to 25° C. The reaction mixture is extracted successively with saturated, aqueous citric acid solution and with saturated aqueous sodium hydrogen carbonate solution, dried over sodium sulphate and concentrated under reduced pressure. In this fashion, 27.97 g of a product, which consists to 80% of the S enantiomer of the formula (VIII-2), are obtained. The yield accordingly works out at 71% of theory.

The product is further reacted without additional purification.

IR spectrum (NaCl): OH bands at 3,540 cm$^{-1}$. R—SO$_2$—OR: 1345 cm$^{-1}$ and 1175 cm$^{-1}$.

4th stage

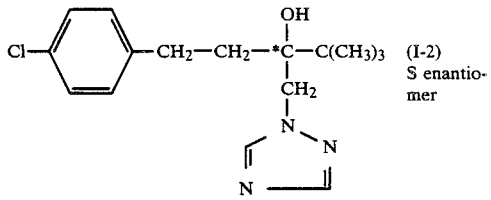

A mixture of 27.3 g (81.5 mmol) of the S enantiomer of the compound of the formula (VIII-2), 22.3 g (240 mmol) of the sodium salt of triazole and 100 liters of dimethyl formamide is stirred for 6 hours at 120° C. under a nitrogen atmosphere. The mixture is then concentrated under reduced pressure, and the residue remaining is added to a mixture of water and methylene chloride. The organic phase is separated off, the aqueous phase is extracted twice with methylene chloride, and the combined organic phases are dried over sodium sulphate and concentrated. 33.0 g of a product, which is purified by column chromatography on 1,000 g of silica gel using a mixture of methylene chloride/methanol=95:5 as eluant, remain.

12.4 g of a product which, according to gas-chromatographic analysis, consists to 95% of the S enantiomer of 2,2-dimethyl-5-(4-chlorophenyl)-3-(1,2,4-triazole-1-yl-methyl)-pentan-3-ole, are obtained by concentrating the eluate. From this, the yield works out at 37% of theory, relative to the S diasteromer of the formula (IV-2).

[α]$_D^{20}$= −34.0° (c=1, CHCl$_3$).

Optical purity≧85% e.e.

Content of S enantiomer≦7%.

Mass spectrum: (ci) m/e=308 (100%, M$^+$+H).

$^1$H NMR spectrum (360 MHz, CDCl$_3$): $\sigma$=1.04 (s, 9H, tert.-butyl) 1.70–2.00 (m, 2H,

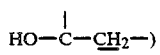

2.30–2.60 (m, 2H—CH$_2$—Ph—Cl) 3.37 (s, 1H, —OH) 4.35 (s, 2H, —CH$_2$—triazole) 6.90–7.30 (m, 4H, aromat. H) 8.00 and 8.35 (each s, each 1H, triazole-H).

Preparation of the starting material of the formula

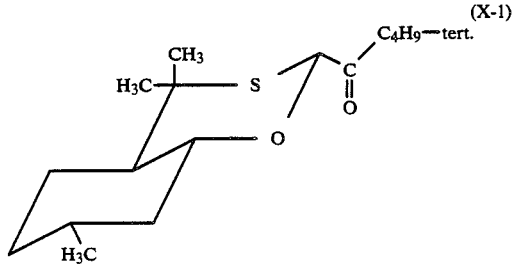

100 ml (0.20 mol) of n-butyllithium in n-hexane (2.0 molar) are added at −78° C. under a nitrogen atmosphere to a solution of 40 g (0.20 mol) of oxathiane compound of the formula (III-1) in 150 ml of absolute tetrahydrofuran. The solution is warmed briefly to 0° C., then recooled to −78° C., a solution of 22.2 g (0.26 mol) of pivaldehyde in 50 ml of absolute tetrahydrofuran is added dropwise at this temperature, and the reaction mixture is then warmed slowly to room temperature and stirred for a further 30 minutes at 25° C. The work-up is effected in the fashion as specified in Example 1, first stage. 57.3 g (100% of theory) of the product of the formula

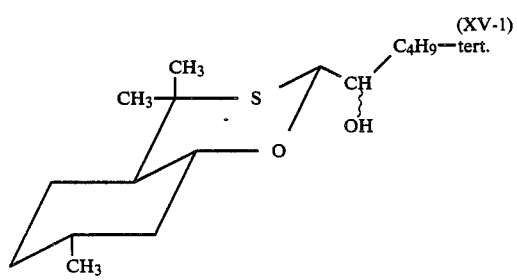

are obtained in the form of a 60:40 mixture of the diastereomers.

IR spectrum (NaCl).

OH bands at 3,600–3,200 cm$^{-1}$.

A solution of 40.5 g (0.19 mol) of trifluoroacetic anhydride in 50 ml of absolute methylene chloride is added dropwise at −78° C. under a nitrogen atmosphere and with stirring to a solution of 14.8 g (0.19 mol) of absolute dimethyl sulphoxide in 100 ml of absolute methylene chloride. The mixture is stirred for a further 15 minutes at −78° C., a solution of 51.3 g (0.18 mol) of the product of the formula (XV-1) in 50 ml of absolute methylene chloride is then added dropwise, the mixture is stirred for 1 hour at −78° C., 61 ml (0.44 mol) of triethylamine are then added dropwise at −78° C., and the mixture is warmed slowly to 0° C. For work-up, the reaction mixture is poured into 500 ml of 5% strength aqueous hydrochloric acid. The organic phase is separated off, the aqueous phase is extracted with methylene chloride, and the combined organic phases are washed once with aqueous sodium chloride solution, dried over sodium sulphate and concentrated under reduced pressure. The easily volatile components are distilled off by brief warming to 100° C. under a pressure of 0.1 mbar. 36.4 g (64% of theory) of the compound of the formula (X-1) are obtained in this fashion.

IR spectrum (KBr):

CO bands at 1,700 cm$^{-1}$.

$^1$H NMR spectrum (360 MHz, CDCl$_3$): σ=0.92 (d, 3H,

|
C̲H$_3$—CH—)

1.24 (s, 9H, tert.-butyl) 1.29 and 1.47 (each s, each 3H, C̲H$_3$—C—C̲H$_3$) 3.45 (d of t, 1H, —C̲H—OR) 5.80 (s, 1H,

|
—S—C̲H—O—)

Preparation of further starting materials:

EXAMPLE 3

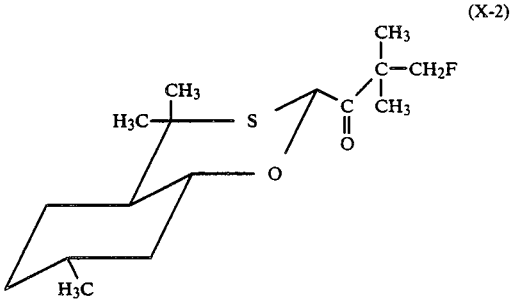

A solution of 39.7 g (81 mmol) of n-butyl-lithium (2.05 mol) in n-hexane is added at −78° C. under a nitrogen atmosphere with stirring to a solution of 16.32 g (81.5 mmol) of the oxathiane of the formula (III-1) in 100 ml of absolute tetrahydrofuran. The reaction mixture is warmed briefly to 0° C. and recooled to −78° C.

A solution of 11.1 g (106 mmol) of monofluoropivaldehyde in 25 ml of absolute tetrahydrofuran is added dropwise at this temperature, and the mixture is warmed slowly to 25° C. and stirred for a further 30 minutes at 25° C. The work-up is effected in the fashion specified in Example 1, first stage. 24.66 g (100% of theory) of the product of the formula

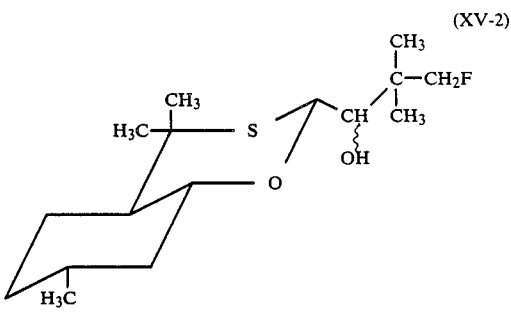

are obtained in the form of a mixture of diastereomers in which the ratio of these diastereomers is 56:44.

IR spectrum (NaCl):

OH bands at 3,600–3,200 cm$^{-1}$.

A solution of 22.45 g (107 mmol) of trifluoroacetic anhydride in 50 ml of absolute methylene chloride is added dropwise at −78° C. under a nitrogen atmosphere and with stirring to a solution of 8.50 g (109 mmol) of absolute dimethyl sulphoxide in 50 ml of absolute methylene chloride. The mixture is stirred for a further 15 minutes at −78° C., a solution of 29.9 g (99 mmol) of the product of the formula (XV-2) in 50 ml of absolute methylene chloride is then added dropwise, the mixture is stirred for 1 hour at −78° C., 34.3 ml (248 mmol) of triethylamine are then added dropwise at −78° C., and the mixture is warmed slowly to 0° C. For work-up, the reaction mixture is poured into 500 ml of 5% strength aqueous hydrochloric acid. The organic phase is separated off, the aqueous phase is extracted with methylene chloride, and the combined organic phases are washed once with aqueous sodium chloride solution, dried over sodium sulphate and concentrated under reduced pressure. The easily volatile components are removed by distillation by heating briefly to 100° C. under a pressure of 0.1 mbar. 22.92 g (77% of theory) of the compound of the formula (X-2) are obtained in this fashion.

IR spectrum (NaCl):
CO bands at 1,720 cm$^{-1}$.
$^1$H NMR spectrum (360 MHz, CDCl$_3$) σ=0.93 (d, 3H,

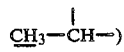
CH$_3$—CH—)

1.27, 1.30 and 1.47 (each s, each 3H, CH$_3$—) 3.48 (m, 1H,

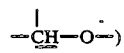
—CH—O—)

4.50 (m, 2H, —CH$_2$F) 5.78 (s, 1H,

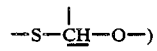
—S—CH—O—)

mmol) of the oxathiane ketone of the formula (X-2) in 10 ml of absolute ether is added dropwise at this temperature.

The reaction mixture is warmed slowly to room temperature and refluxed for a further 4 hours. For workup, the reaction mixture is poured into 100 ml of aqueous ammonium chloride solution, the organic phase is separated off, and the aqueous phase is extracted three times with methylene chloride, dried over sodium sulphate and concentrated under reduced pressure. A mixture of the two diastereomers of the formula (IV-3) and (IV-4), in which the R:S diastereomer ratio is 95:4.2 (91.6% d.e.), is obtained in quantitative yield.

IR spectrum (NaCl):
OH bands at 3,600–3,200 cm$^{-1}$.
Mass spectrum (Ci): m/e=421 (100%, MH$^+$ —H$_2$O).

EXAMPLE 4

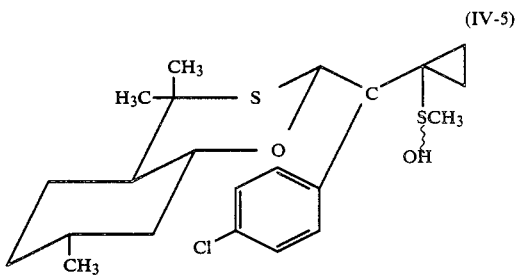
(IV-5)

29.3 ml of n-butyl-lithium in n-hexane (2.05M) are added at −78° C. under a nitrogen atmosphere and with stirring to a solution of 12.00 g (60 mmol) of the oxathiane of the formula (III-1) in 70 ml of absolute tetrahy-

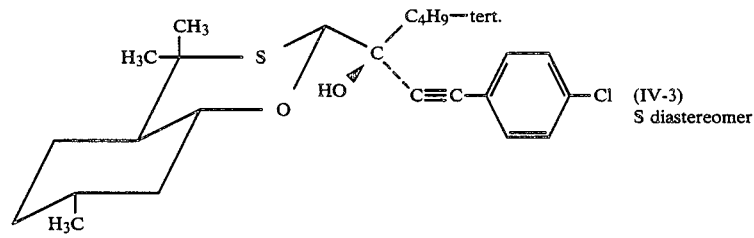
(IV-3) S diastereomer and

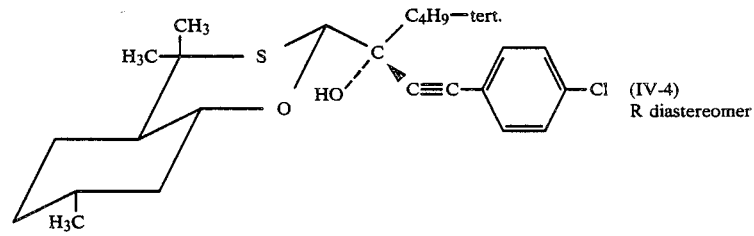
(IV-4) R diastereomer 9.75 ml (20 mmol) of n-butyl-lithium in n-hexane (2.05M) are added dropwise at 0° C. under a nitrogen atmosphere with stirring to a solution of 3.41 g (25 mmol) of 4-chlorophenylacetylene in 20 ml of absolute diethyl ether. After 10 minutes, 5.16 g (20 mmol) of magnesium bromide etherate are added and the mixture is stirred for a further 15 minutes at 0° C. After cooling the reaction mixture to −78° C., a solution of 3.02 g (10 drofuran. The reaction mixture is warmed briefly to 0° C. and recooled to −78° C.

A solution of 13.60 (60 mmol) of 4-chlorophenyl 1-methylmercapto-cycloprop-1-yl ketone in 40 ml of absolute tetrahydrofuran is added dropwise at this temperature, and the mixture is warmed slowly to room temperature and stirred for a further 30 minutes at room temperature. The work-up is effected in the fashion specified in Example 1, first stage. 25.2 g (98% of theory) of a mixture of diastereomers, in which the two diastereomers are present in the ratio 61:39, are obtained.

IR spectrum (NaCl):
OH bands 3,600–3,200 cm$^{-1}$; =CH 3,090 and 3,030 cm$^{-1}$; C=C 1,600 and 1,590 cm$^{-1}$.

The diastereomers are separated by column chromatography on silica gel (eluant: chlorobenzene).

Diastereomer I $^1$H NMR spectrum (360 MHz, CDCl$_3$): σ=2.96 (s, 1H, O—H) 3.59 (m, 1H,

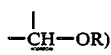

6.10 (s, 1H,

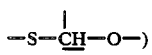

7.25–7.63 (m, 4H, aromat. H).

Diastereomer II

σ=2.87 (s, 1H, —O—H) 3.53 (m, 1H,

6.20 (s, 1H,

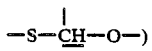

7.25–7.63 (m, 4H, aromat. H).

It will be understood that the specification and examples are illustrative but not limitative of the present invention and that other embodiments within the spirit and scope of the invention will suggest themselves to those skilled in the art.

What is claimed is:

1. A process for the preparation of an optically active 2-hydroxyethyl-azole derivative of the formula

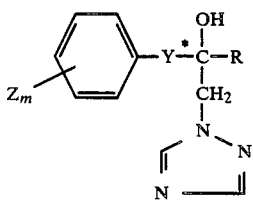

in which
R represents optionally substituted alkyl, optionally substituted cycloalkyl or optionally substituted phenyl,
Y represents the —CH$_2$—CH$_2$—, —CH=CH— or —C≡C— groups, or represents a direct bond,
Z represents halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy, and
m represents the numbers 0, 1, 2 or 3,
comprising
(a) reacting in a first stage, a ketone of the formula

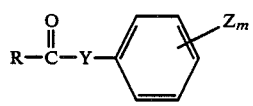

in which
R, Y, Z and m have the abovementioned meaning, with an enantiomerically pure oxathiane of the formula

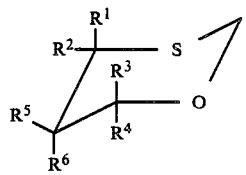

in which
R$^1$, R$^2$, R$^3$, R$^4$, R$^5$ and R$^6$ represent hydrogen or alkyl, but at least one of the radicals represents alkyl, or
R$^4$ and R$^5$, together, represent optionally alkyl-substituted alkanediyl, or
R$^4$ and R$^5$, together with the neighbouring carbon atoms, represent an optionally alkyl-substituted, fused bicyclic hydrocarbon radical,
in the presence of a strongly basic organometallic compound, and in the presence of a diluent, at a temperature between −80° C. and +120° C., then, in a second stage, separating the mixture of diastereomeric compounds of the formulae

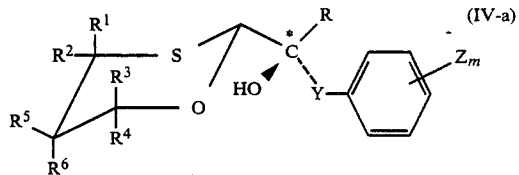

and

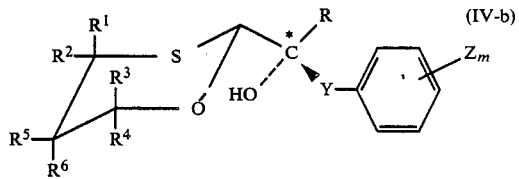

in which
R, R$^1$, R$^2$, R$^3$, R$^4$, R$^5$, R$^6$, Y, Z and m have the abovementioned meaning,
thus obtained as a result of their different physical properties, then, in a third stage, initially reacting the diastereomer of the formula (IV-a) or (IV-b) desired in each case with a reagent which is suitable for the cleavage of an oxathiane compound, in the presence of a diluent at a temperature between 0° C. and 100° C., and then reacting the optically active α-hydroxyaldehyde of the formula

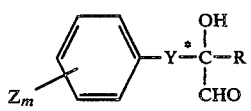 (V)

in which
R, Z, Y and m have the abovementioned meaning, produced during this, with a reagent which is suitable for the reduction of an aldehyde, in the presence of a diluent at a temperature between −20° C. and +100° C., furthermore, in a fourth stage, reacting the optically active diol of the formula

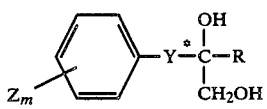 (VI)

in which
R, Y, Z and m have the abovementioned meaning, thus obtained with a sulphonic acid derivative of the formula

 (VII)

R$^7$—SO$_2$—Hal in which
R$^7$ represents alkyl, halogenoalkyl or optionally substituted phenyl, and
Hal represents halogen,
in the presence of a diluent and in the presence of an acid-binding agent at a temperature between 0° C. and 100° C., and finally, in a fifth stage, reacting the resultant optically active compound of the formula

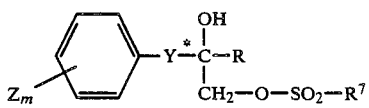 (VIII)

in which
R, R$^7$, Y, Z and m have the abovementioned meaning,
with a triazole salt of the formula

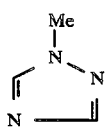 (IX)

in which
Me represents an alkali metal, in the presence of a diluent at a temperature between 20° C. and 150° C.,
or
(b) in a first stage, reacting an enantiomerically pure oxathiane ketone of the formula

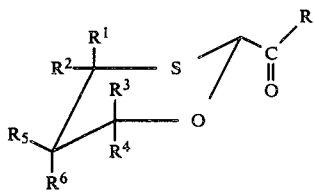 (X)

in which
R, R$^1$, R$^2$, R$^3$, R$^4$, R$^5$ and R$^6$ have the abovementioned meaning,
with an organometallic compound of the formula

 (XI)

in which
Y, Z and m have the abovementioned meaning, and
R$^8$ represents an alkali metal, a transition metal alkylate or a radical of the formula Me$^1$X, in which
Me$^1$ represents an alkaline earth metal or zinc, and
X represents chlorine, bromine or iodine,
in the presence of a diluent at a temperature between −78° C. and +100° C.,
then, in a second stage, initially reacting the diastereomer of the formula

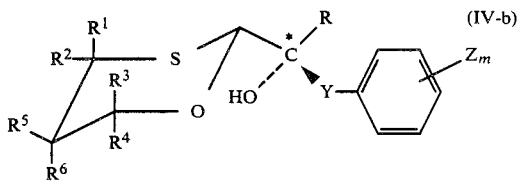 (IV-b)

in which
R, R$^1$, R$^2$, R$^3$, R$^4$, R$^5$, R$^6$, Y, Z and m have the abovementioned meaning,
produced preferentially, with a reagent which is suitable for the cleavage of an oxathiane compound, in the presence of a diluent at a temperature between 0° C. and 100° C., and then carrying out the further procedure in the same fashion as in the case of process version (a), or
(c) in a first stage, reacting an enantiomerically-pure oxathiane ketone of the formula (XII)

in which
R$^1$, R$^2$, R$^3$, R$^4$, R$^5$, R$^6$, Y, Z and m have the abovementioned meaning,
with an organometallic compound of the formula

R—R$^8$ (XIII)

in which

R and R⁸ have the abovementioned meaning, in the presence of a diluent at a temperature between −78° C. and +100° C., then, in a second stage, initially reacting the diastereomer of the formula

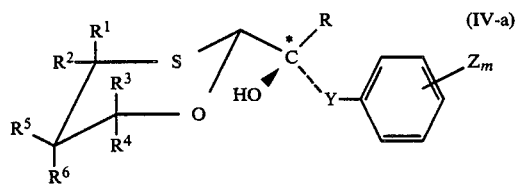

in which

R, R¹, R², R³, R⁴, R⁵, R⁶, Y, Z and m have the abovementioned meaning, produced preferentially, with a reagent which is suitable for the cleavage of an oxathiane compound, in the presence of a diluent at a temperature between 0° C. and 100° C., and then carrying out the further procedure in the same fashion as in the case of process version (a).

2. A process as claimed in claim 1, wherein the starting material employed is a ketone of the formula (II), in which R represents straight-chain or branched alkyl, having 1 to 6 carbon atoms, which is optionally substituted by halogen, alkoxy having 1 to 4 carbon atoms, alkylthio having 1 to 4 carbon atoms, the formyl group and derivatives thereof, phenoxy and/or phenyl, cycloalkyl, having 3 to 8 carbon atoms, which is optionally substituted by alkyl having 1 to 4 carbon atoms, alkoxy having 1 to 4 carbon atoms, alkylthio having 1 to 4 carbon atoms and/or halogen, or phenyl which is optionally substituted by alkyl having 1 to 4 carbon atoms, alkoxy having 1 to 4 carbon atoms, alkylthio having 1 to 4 carbon atoms and/or halogen, Y represents the —CH₂—CH₂—, —CH=CH— or —C≡C— groups or represents a direct bond, Z represents fluorine, chlorine, bromine, alkyl having 1 to 4 carbon atoms, cycloalkyl having 3 to 8 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, phenyl which is optionally substituted by halogen and/or alkyl having 1 to 4 carbon atoms, phenoxy which is optionally substituted by halogen and/or alkyl having 1 to 4 carbon atoms, phenylalkyl, having 1 or 2 carbon atoms in the alkyl part, which is optionally substituted by halogen and/or alkyl having 1 to 4 carbon atoms, or phenylalkoxy, having 1 or 2 carbon atoms in the alkoxy part, which is optionally substituted by halogen and/or alkyl having 1 to 4 carbon atoms, and m represents the numbers 0, 1, 2 or 3.

3. A process as claimed in claim 1, wherein the starting material is the ketone of the formula

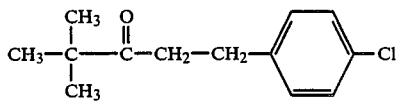

4. A process according to claim 1, wherein the enantiomerically pure oxathiane is a compound of the formula (III) in which R¹, R², R³, R⁴, R⁵ and R⁶ represent hydrogen or alkyl having 1 to 4 carbo atoms, but where at least one of these radicals represents alkyl having 1 to 4 carbon atoms, or R⁴ and R⁵, together, alternatively represent alkanediyl, having 3 to 6 carbon atoms, which is optionally mono- to trisubstituted, identically or differently, by alkyl having 1 to 4 carbon atoms, or alternatively R⁴ and R⁵, together with the neighbouring carbon atoms, represent an anellated bicyclic hydrocarbon, having 7 or 8 carbon atoms, which is optionally mono- to trisubstituted by alkyl having 1 to 4 carbon atoms, the substituents being identical or different.

5. A process as claimed in claim 1, wherein the enantiomerically pure oxathiane is the compound of of the formula

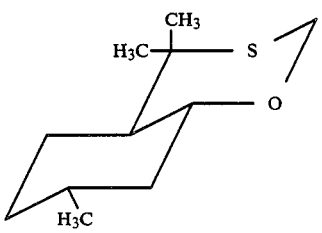

6. A process as claimed in claim 1, wherein the enantiomerically pure oxathiane ketone of the formula (X) is the compound of the formula

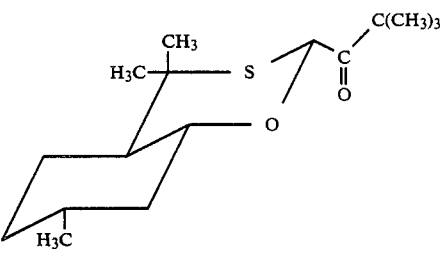

7. A process as claimed in claim 1, wherein the enantiomerically pure oxathiane ketone of the formula (XII) is the compound of the formula

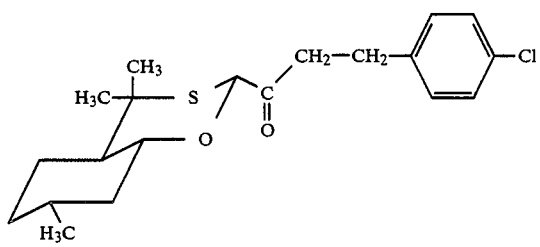

* * * * *